United States Patent [19]

Suzuki et al.

[11] Patent Number: 5,326,889
[45] Date of Patent: Jul. 5, 1994

[54] PROCESS FOR PRODUCING 1,4-BUTANEDIOL AND TETRAHYDROFURAN

[75] Inventors: Sadakatsu Suzuki; Tatsumi Ichiki; Hiroshi Ueno, all of Saitama, Japan

[73] Assignee: Tonen Corporation, Tokyo, Japan

[21] Appl. No.: 971,495

[22] Filed: Nov. 4, 1992

Related U.S. Application Data

[62] Division of Ser. No. 807,974, Dec. 16, 1991, abandoned, which is a division of Ser. No. 616,488, Nov. 21, 1990, Pat. No. 5,099,038.

[30] Foreign Application Priority Data

Dec. 7, 1989 [JP] Japan .................................. 1-316474

[51] Int. Cl.$^5$ ..................... C07D 307/08; C07D 27/06
[52] U.S. Cl. .................................. 549/508; 568/864; 568/885
[58] Field of Search ................ 549/295, 508; 568/864, 568/885

[56] References Cited

U.S. PATENT DOCUMENTS

| 2,130,501 | 9/1938 | Lazier | 549/508 |
| 4,006,104 | 2/1977 | Michalczyk et al. | 549/508 |
| 4,977,284 | 12/1990 | Suzuki et al. | 549/508 |

FOREIGN PATENT DOCUMENTS

| 7409463 | 3/1974 | Japan | 549/508 |
| 7501038 | 1/1975 | Japan | 549/508 |

Primary Examiner—C. Warren Ivy
Assistant Examiner—Ba K. Trinh
Attorney, Agent, or Firm—John J. Mahon

[57] ABSTRACT

There is disclosed a process for the production of 1,4-butanediol and tetrahydrofuran by the catalytic hydrogenation in the gas phase of γ-butyrolactone using a solid catalyst comprising copper and silicon, copper, chromium, and manganese or copper, chromium, manganese and barium.

1 Claim, No Drawings

PROCESS FOR PRODUCING 1,4-BUTANEDIOL AND TETRAHYDROFURAN

This is a division of application Ser. No. 807,974, filed Dec. 16, 1991, now abandoned, which is a Rule 60 divisional of U.S. Ser. No. 616,488, filed Nov. 21, 1990, which is based on Japanese Patent Application No. 316474/89, filed Dec. 7, 1989, now U.S. Pat. No. 5,099,038.

The present invention relates to a process for producing 1,4-butanediol and tetrahydrofuran. More particularly, the present invention relates to a process for producing 1,4-butanediol and tetrahydrofuran by the catalytic hydrogenation of γ-butyrolactone which is performed in gas phase in the presence of a specific catalyst. According to a preferred embodiment, the γ-butyrolactone is produced by the catalytic hydrogenation of maleic anhydride which is performed in liquid phase in the presence of a catalyst.

PRIOR ART

Since 1,4-butanediol is a useful compound as a raw material for polybutylene terephthalate resin and polyurethane resin, there has been a strong demand for a process for producing it efficiently and economically.

There are know processes (as explained below) for producing 1,4-butanediol by the catalytic hydrogenation of maleic anhydride and/or succinic anhydride or a derivative thereof.

(a) A process for producing 1,4-butanediol by the hydrogenation of maleic anhydride and/or maleic acid in liquid phase in the presence of a catalyst containing an element (or a compound thereof) belonging to the VII subgroup and VIII subgroup of the periodic table. (Japanese Patent Laid-open No. 133212/1976)

(b) A process for producing 1,4-butanediol by the hydrogenative decomposition of maleic acid diester or fumaric acid diester in gas phase in the presence of a copper chromite catalyst. (Japanese Patent Laid-open No. 22035/1986 and Japanese Patent Published Publication No. 501702/1987)

The present inventors also proposed a process for producing 1,4-butanediol by the catalytic hydrogenation of maleic anhydride and/or succinic anhydride in gas phase in the presence of a copper oxide-zinc oxide catalyst. (Japanese Patent Application No. 175062/1988)

There are also known processes (as explained below) for producing γ-butyrolactone by the catalytic hydrogenation of maleic anhydride and/or succinic anhydride in liquid phase or gas phase.

(c) A process for producing γ-butyrolactone by the catalytic hydrogenation of maleic anhydride in liquid phase in the presence of a nickel catalyst. (Japanese Patent Publication No. 6946/11968)

(d) A process for producing γ-butyrolactone and tetrahydrofuran by the catalytic hydrogenation of maleic anhydride in the presence of a nickel catalyst in combination with rhenium or a rhenium compound. (Japanese Patent Publication No. 6947/1986)

(e) A process for producing γ-butyrolactone and/or tetrahydrofuran by the hydrogenation of maleic anhydride and/or succinic anhydride in liquid phase in the presence of a solid catalyst composed of palladium, cobalt, and niobium. (Japanese Patent Laid-open No. 111975/1987)

On the other hand, tetrahydrofuran (as well as 1,4-butanediol) is also a useful compound as a raw material for polytetramethylene glycol and as a solvent for polyvinyl chloride and polyurethane; therefore, there has been a strong demand for a process for producing it efficiently and economically.

There are known processes (as explained below) for producing 1,4-butanediol and/or tetrahydrofuran by the catalytic hydrogenation of γ-butyrolactone in gas phase.

(f) A process for producing 1,4-butanediol and tetrahydrofuran by the hydrogenative decomposition of γ-butyrolactone in gas phase in the presence of a catalyst which is a mixture formed by reducing copper oxide and zinc oxide. (Japanese Patent Published Publication No. 500993/1983)

(g) A process for producing 1,4-butanediol by the catalytic hydrogenation of γ-butyrolactone in gas phase in the presence of a copper chromite catalyst. (Japanese Patent Laid-open No. 155231/1987)

(h) A process for producing tetrahydrofuran and 1,4-butanediol by the one-stage catalytic hydrogenation of maleic anhydride and/or succinic anhydride in gas phase in the presence of a solid catalyst containing copper, chromium, and manganese. (Japanese Patent Application No. 313760/1988 filed by the present inventors)

Problems to be Solved by the Invention

There are some problems involved in the abovementioned known processes (a) and (b) for producing 1,4-butanediol by the catalytic hydrogenation of maleic anhydride and/or succinic anhydride or a derivative thereof. In other words, the hydrogenation of maleic anhydride and/or maleic acid in liquid phase in the presence of a catalyst requires a high pressure of about 200 kg/cm$^2$. This leads to a huge amount of equipment cost and running cost. On the other hand, the hydrogenative decomposition of maleic acid diester in gas phase in the presence of a catalyst does not need the high pressure as mentioned above; however, it needs additional process for diesterifying maleic anhydride, which makes the process very complex. That is to say, the reaction to convert a monoester into a diester (which is an equilibrium reaction) needs two stages for its completion. Thus the entire reaction needs three stages, namely, two stages for diesterification and one stage for monoesterification.

There is an advantage of not requiring high pressure and complex equipment in the process (h) (mentioned above and proposed by the present inventors) for producing 1,4-butanediol by the catalytic hydrogenation of maleic anhydride and/or succinic anhydride in gas phase in the presence of a catalyst. However, this advantage is set by a disadvantage that the reaction to form 1,4-butanediol is so slow that the process is poor in space time yield.

There are also some problems involved in the above-mentioned known processes (f) and (g) for producing 1,4-butanediol and/or tetrahydrofuran by the catalytic hydrogenation of γ-butyrolactone in gas phase. That is to say, they are unable to control as desired the ratio between 1,4-butanediol and tetrahydrofuran to be produced.

It is an object of the present invention to provide an improved process for producing 1,4-butanediol and/or tetrahydrofuran by the catalytic hydrogenation of γ-butyrolactone in gas phase, wherein the improvement includes the usage of a specific catalyst which increases the conversion ratio of γ-butyrolactone and facilitates control over the ratio between 1,4-butanediol and tetrahydrofuran to be produced.

It is another object of the present invention to provide an improved process for producing 1,4-butanediol and tetrahydrofuran simultaneously from maleic anhydride economically in a high space time yield, unlike the conventional complex process which needs a high equipment cost and running cost.

Means to Solve the Problems

SUMMARY OF THE INVENTION

The present inventors carried out extensive studies in search of a catalytic hydrogenation of maleic anhydride which would give 1,4-butanediol and tetrahydrofuran in a high space time yield at as low a pressure as possible. As the result, it was found that the object is achieved by performing the catalytic hydrogenation in two stages, namely, the first stage for converting maleic anhydride into γ-butyrolactone and the second stage for converting γ-butyrolactone into 1,4-butanediol and tetrahydrofuran. It was also found that the second stage of the catalytic hydrogenation should be performed in gas phase in the presence of a specific catalyst.

The present invention relates to a process for producing 1,4-butanediol and tetrahydrofuran by the catalytic hydrogenation of γ-butyrolactone in gas phase in the presence of a solid catalyst containing copper and silicon, or containing copper, chromium, and manganese, or containing copper, chromium, manganese, and barium. A preferred embodiment of the present invention consists of subjecting maleic anhydride to catalytic hydrogenation in liquid phase in the presence of a catalyst, thereby forming γ-butyrolactone, and subsequently subjecting the γ-butyrolactone to catalytic hydrogenation in gas phase in the presence of a solid catalyst containing copper and silicon, or containing copper, chromium, and manganese, or containing copper, chromium, manganese, and barium. The catalytic hydrogenation of maleic anhydride into 1,4-butanediol and tetrahydrofuran proceeds through the following path.

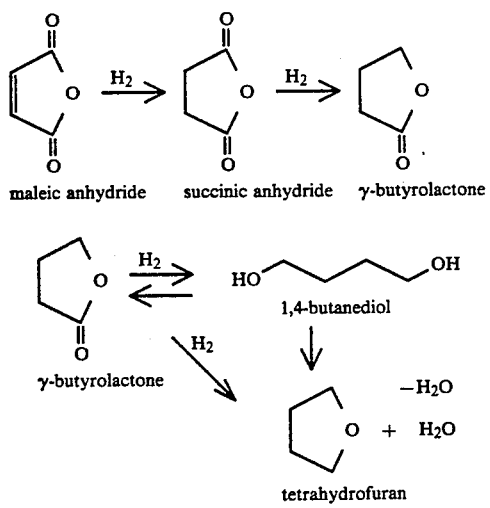

According to a preferred embodiment of the present invention, the catalytic hydrogenation (I) of maleic anhydride into γ-butyrolactone is carried out in liquid phase at as low a pressure as possible to avoid problems involved in the gas phase reaction, and the catalytic hydrogenation (II) of γ-butyrolactone into 1,4-butanediol and tetrahydrofuran is carried out in gas phase at as high a pressure as possible within a limit to keep a high ratio between hydrogen and γ-butyrolactone in gas phase. In this way, the equilibrium reaction (II) proceeds to give 1,4-butanediol and tetrahydrofuran advantageously.

In what follows, the present invention will be explained with reference to an embodiment which consists of producing the desired products from maleic anhydride in two stages. This embodiment is not intended to restrict the scope of the present invention.

Production of γ-butyrolactone by Liquid Phase Process

In this embodiment, the first stage of the reaction consists of producing γ-butyrolactone from maleic anhydride by catalytic hydrogenation in liquid phase.

Catalyst

The first stage of the reaction in liquid phase needs a catalyst which may be a known nickel catalyst, a nickel catalyst incorporated with rhenium or a rhenium compound, or a solid catalyst composed of palladium, cobalt, and niobium. It is possible to use an alternative catalyst which is prepared by reducing a commercial copper oxide-chromium oxide-manganese oxide catalyst or a commercial nickel oxide-copper oxide-cobalt oxide catalyst.

The reduction of a commercial catalyst may be accomplished by treating the catalyst with a nitrogen gas containing hydrogen. To perform the treatment, a nitrogen gas containing 2 vol % of hydrogen is passed through the catalyst bed at a gas hourly space velocity (G.H.S.V.) of about 2400 $h^{-1}$ under a pressure of tens of $kg/cm^2 G$ at 170° C. for 24 hours. The treatment is continued for several hours, with the hydrogen content gradually increased to 100 vol % and the temperature of the catalyst bed raised to 200° C. (G.H.S.V. is expressed in terms of normal temperature and normal pressure hereinafter.)

Solvent

The solvent used for the above-mentioned liquid phase reaction is not specifically limited. It includes, for example, γ-butyrolactone, tetrahydrofuran, dimethyl ether, diethyl ether, 1,4-dioxane, benzene, and toluene. The solvent may be omitted.

Conditions of Catalytic Reaction

In the above-mentioned liquid phase reaction to be performed in the first stage, the gas-liquid mixed phase (composed of maleic anhydride and hydrogen gas) is brought into contact with the catalyst by any known method using a fixed bed reactor, moving bed reactor, or fluidized bed reactor. This stage of reaction may also be carried out batchwise. The continuous operation should be carried out so that the gas-liquid mixed phase (composed of maleic anhydride and hydrogen gas) is passed through the catalyst at an LHSV of 0.001–1.0 $h^{-1}$. The batchwise operation should be carried out so that the reaction continues for 0.5–16 hours. In either cases, the reaction temperature should be about 150°–300° C. and the reaction pressure should be about 60–150 $kg/cm^2 G$.

The liquid phase reaction in the first stage gives rise to a reaction product which varies depending on the catalyst, reaction temperature, and reaction pressure employed. Usually, it is composed of 50-95 mol % of γ-butyrolactone, 1-30 mol % of tetrahydrofuran, 0.5-5 mol % of n-butanol, and 0-10 mol % of succinic anhydride.

Production of 1,4-Butanediol and Tetrahydrofuran by Gas Phase Process

According to the process of the present invention, 1,4-butanediol and tetrahydrofuran are produced from γ-butyrolactone by the catalytic hydrogenation in gas phase. The γ-butyrolactone as the starting material may be the reaction product obtained in the above-mentioned liquid phase reaction. The reaction product may be used as such or after purification. This gas phase reaction corresponds to the second stage of reaction in the abovementioned embodiment.

Catalyst

The second stage of the reaction in gas phase needs a catalyst which may be formed by reducing a copper oxide-silicon oxide catalyst, copper oxide-chromium oxide-manganese oxide catalyst, or copper oxide-chromium oxide-manganese oxide-barium oxide catalyst. The preparation of the catalyst may be performed in the following manner, which is explained with reference to a copper oxide-silicon oxide catalyst. First, copper nitrate (or any other copper compound) is dissolved in water. To the resulting aqueous solution is added pulverized silicon oxide (such as silica, silica gel, silica sol). The mixture is neutralized with an aqueous solution of sodium carbonate which is added dropwise while the mixture is heated and stirred. Solids are filtered off and dried. Finally, the dried solids are calcinated and molded into a desired shape using a molding machine. The thus obtained catalyst is reduced in the same manner as used for the preparation of the catalyst for the liquid phase reaction.

Solvent

The solvent used for the gas phase reaction in the present invention is not specifically limited. It includes, for example, γ-butyrolactone, tetrahydrofuran, dimethyl ether, diethyl ether, 1,4-dioxane, benzene, and toluene. The solvent may be omitted.

Conditions of Catalytic Reaction

In the above-mentioned gas phase reaction to be performed in the second stage, the mixed gas (composed of γ-butyrolactone and hydrogen gas) is brought into contact with the catalyst by any known method using a fixed bed reactor moving bed reactor, or fluidized bed reactor. This stage of reaction may also be carried out batchwise. The reaction should be carried out so that the mixed gas (composed of γ-butyrolactone and hydrogen gas) comes into contact with the catalyst at a G.H.S.V. of 1000-100000 $h^{-1}$, preferably 3000-40000 $h^{-1}$. The reaction temperature should be about 150°-280° C. and the reaction pressure should be about 10-100 kg/cm$^2$G. The molar ratio of hydrogen gas to γ-butyrolactone is 50-1500. An adequate reaction temperature, reaction pressure, and molar ratio should be selected so that the system remains in gas phase. With a hydrogen/γ-butyrolactone molar ratio lower than 50, the reaction is slow and the catalyst is degraded by a carbonaceous substance which forms during the reaction. Conversely, with a molar ratio higher than 1500, the reaction is economically disadvantageous because of the necessity of circulating a large amount of hydrogen.

The gas phase reaction in the second stage gives rise to 1,4-butanediol and tetrahydrofuran in a varied ratio depending on the reaction pressure and reaction temperature. Usually, the molar ratio of tetrahydrofuran to 1,4-butanediol is in the range of 0.05 to 200. The reaction product can be easily separated into 1,4-butanediol and tetrahydrofuran by any known method such as distillation.

Effect of the Invention

According to the present invention, maleic anhydride is made into γ-butyrolactone by the liquid-phase reaction which poses no problems such as coking. In addition, this reaction can be performed at a much lower pressure than the conventional process for converting maleic anhydride directly into 1,4-butanediol. The low pressure leads to the reduction of equipment cost and running cost. The thus obtained γ-butyrolactone is subsequently made into 1,4-butanediol and tetrahydrofuran by the gas phase reaction. Since this gas phase reaction is an equilibrium reaction, it is possible to obtain 1,4-butanediol and tetrahydrofuran in a high space time yield, and it is also possible to control the ratio between 1,4-butanediol and tetrahydrofuran, if proper reaction conditions are chosen.

The process of the present invention is economical because the reaction product in the liquid phase reaction (first stage) can be supplied without purification to the gas phase reaction (second stage). According to the present invention, the reaction is performed in two stages. This offers an advantage that the reaction does not form a polyester as a by-product because the reaction system does not contain maleic anhydride or succinic anhydride as a raw material and 1,4-butanediol as a reaction product at the same time.

The invention will be explained with reference to the following examples, which are not intended to restrict the scope of the invention. In the examples, percentage (%) is based on weight, unless otherwise indicated.

EXAMPLE 1

Preparation of γ-Butyrolactone)

The catalyst for the catalytic hydrogenation was prepared by reducing in the following manner a commercial copper oxide-chromium oxide-manganese oxide catalyst (G-89, powder type, a product of Nissan Gardlar Shokubai Co., Ltd.) containing 38.9% of copper, 37.3% of chromium, and 3.6% of manganese. First, the commercial catalyst was heated at 170° C. under a nitrogen stream at a pressure of 40 kg/cm$^2$G. Hydrogen was slowly added to the nitrogen stream until the hydrogen content reached 2 vol %. The nitrogen stream containing 2 vol % of hydrogen was passed through the catalyst overnight at 170° C. and 40 kg/cm$^2$G, with the G.H.S.V. being 2400 $h^{-1}$. The hydrogen content in the nitrogen stream was gradually increased to 100 vol %, while keeping the catalyst bed lower than 200° C. Finally, the reduction with hydrogen was performed at 200° C. and 40 kg/cm$^2$G for 2 hours, with the G.H.S.V. being 2400 $h^{-1}$.

In a 300-cc stainless steel autoclave equipped with an electromagnetic induction stirrer were placed 100 g of maleic anhydride and 120 g of 1,4-dioxane as a solvent. With the atmosphere in the autoclave replaced with nitrogen, 30 g of the reduced catalyst was placed in the autoclave in such a manner that the catalyst was not exposed to air. Hydrogen was forced into the autoclave, and the catalytic hydrogenation was carried out in liquid phase at 220° C. and 90 kg/cm²G, for 4 hours.

There was obtained a reaction product composed of 86.5 mol % of γ-butyrolactone, 6.2 mol % of tetrahydrofuran, 2.3 mol % of n-butanol, and 1.4 mol % of succinic anhydride. The conversion of maleic anhydride was 100%.

EXAMPLE 2

Preparation of γ-Butyrolactone)

The catalytic hydrogenation of maleic anhydride in liquid phase was carried out in the same manner as Example 1, except that the catalyst was replaced by a commercial nickel catalyst containing 22% of nickel as metal (G53D, a product of Nissan Gardlar Shokubai Co., Ltd.), the 1,4-dioxane as a solvent was replaced by γ-butyrolactone, and the reaction temperature was changed to 240° C.

There was obtained a reaction product composed of 76.4 mol % of γ-butyrolactone, 15.6 mol % of tetrahydrofuran, 3.1 mol % of n-butanol, 0.7 mol % of succinic anhydride, and trace amounts of propionic acid and lactic acid. The conversion of maleic anhydride was 100%.

EXAMPLE 3

The catalyst for the catalytic hydrogenation was prepared by reducing in the same manner as in Example 1 a commercial copper oxide-silicon oxide catalyst (T-366, a product of Nissan Gardlar Shokubai Co., Ltd.) containing 50.6% of copper and 12.4% of silicon in a fixed bed reactor.

With the fixed bed reactor heated to 210° C., the catalytic hydrogenation in gas phase was performed by passing the raw material (which is the reaction product obtained in Example 1), together with 100 times (in mol) as much hydrogen as the raw material, under a pressure of 15 kg/cm²G and at a G.H.S.V. of 4800 h⁻¹.

There was obtained a reaction product composed of 95.2 mol % of tetrahydrofuran and 4.6 mol % of n-butanol. The conversion of γ-butyrolactone was 100%.

EXAMPLE 4

The catalyst for the catalytic hydrogenation was prepared by reducing in the same manner as in Example 1 the same commercial catalyst (pellet type) as used in Example 1. The catalytic hydrogenation in gas phase was performed by passing the raw material (which is the reaction product obtained in Example 2), together with 300 times (in mol) as much hydrogen as the raw material. The reaction temperature was 180° C., the reaction pressure was 40 kg/cm²G, and the G.H.S.V. was 36000 h⁻¹.

There was obtained a reaction product composed of 17 mol % of γ-butyrolactone, 66 mol % of 1,4-butanediol, and 13 mol % of tetrahydrofuran. The conversion of γ-butyrolactone was 78%.

EXAMPLE 5

The catalyst for the catalytic hydrogenation was prepared by reducing in the same manner as in Example 1 a commercial copper oxide-chromium oxide catalyst (N201, a product of Nikki Kagaku Co., Ltd.) containing 27.6% of copper, 31.2% of chromium, 2.5% of manganese, and 0.6% of barium, which had been placed in a fixed bed reactor.

Using this catalyst, the catalytic hydrogenation was performed in gas phase on the reaction product obtained in Example 2, in the same manner as in Example 4 except that the reaction pressure was changed to 60 kg/cm²G and the reaction temperature was changed to 210° C.

There was obtained a reaction product composed of 66 mol % of 1,4-butanediol, 9 mol % of tetrahydrofuran, 21 mol % of γ-butyrolactone, and 3.7 mol % of n-butanol. The conversion of γ-butyrolactone was 73%.

EXAMPLE 6 FOR COMPARISON

The reduction of the catalyst and the catalytic hydrogenation were carried out under the same conditions as in Example 5, except that the commercial catalyst was replaced by a commercial nickel-copper-cobalt catalyst containing 45% of nickel, 4.5% of copper, and 5.0% of cobalt (G-98B, a product of Nissan Gardlar Shokubai Co., Ltd.)

It was found that the reaction product contains merely 2.6 mol % of tetrahydrofuran and contains no γ-butyrolactone and 1,4-butanediol at all. This is because the decomposition reaction was dominant.

REFERENTIAL EXAMPLE

The catalyst for the catalytic hydrogenation was prepared by reducing in the same manner as in Example 1 the same catalyst as used in Example 4. The catalytic hydrogenation in gas phase was performed in a single stage by passing the raw material (which is a solution of maleic anhydride (1 mol) in γ-butyrolactone (1 mol)), together with 200 times (in mol) as much hydrogen as the raw material. The reaction temperature was 180° C., the reaction pressure was 40 kg/cm²G, and the G.H.S.V. was. 9000 h⁻¹.

There was obtained a reaction product composed of 15.1 mol % of 1,4-butanediol, 2.8 mol % of tetrahydrofuran, 81.9 mol % of γ-butyrolactone, and 0.3 mol % of n-butanol. The conversion of maleic anhydride was 100%.

What is claimed is:

1. A two stage process for preparing 1,4-butanediol and tetrahydrofuran which comprises in a first stage converting maleic anhydride into a reaction product comprising 50–95 mol % gamma-butyrolactone, 1–30 mol % tetrahydrofuran, 0.5–5 mol % n-butanol and 0–10 mol % succinic anhydride in a liquid phase hydrogenation process at 150°–300° C. and a pressure of 60–150 kg/cm²G using a catalyst being either a nickel catalyst, a nickel catalyst incorporated with rhenium or a rhenium compound or a catalyst composed of palladium, cobalt and niobium, and a second stage which comprises catalytically hydrogenating the unpurified reaction product of the first stage in the gas phase at a temperature of 150° C.–250° C. and a pressure of 10–100 kg/cm²G and a molar ratio of H$_2$ to gamma-butyrolactone of 50–1500 and in the presence of a solid catalyst containing (i) copper, chromium and manganese or (ii) copper, chromium, manganese and barium to produce a reaction product wherein the molar ratio of tetrahydrofuran to 1,4-butanediol is in the range of 0.05 to 200.

* * * * *